United States Patent
Dorier et al.

(10) Patent No.: US 9,127,982 B2
(45) Date of Patent: Sep. 8, 2015

(54) SPARK CHAMBER FOR OPTICAL EMISSION ANALYSIS

(75) Inventors: Jean-Luc Dorier, Bussigny (CH); Fabio DeMarco, Lausanne (CH); Edmund Halasz, Orbe (CH)

(73) Assignee: THERMO FISHER SCIENTIFIC (ECUBLENS) SARL, Ecublens (CH)

( * ) Notice: Subject to any disclaimer, the term of this patent is extended or adjusted under 35 U.S.C. 154(b) by 209 days.

(21) Appl. No.: 13/817,001

(22) PCT Filed: Aug. 22, 2011

(86) PCT No.: PCT/EP2011/064392
§ 371 (c)(1),
(2), (4) Date: Feb. 14, 2013

(87) PCT Pub. No.: WO2012/028484
PCT Pub. Date: Mar. 8, 2012

(65) Prior Publication Data
US 2013/0148118 A1  Jun. 13, 2013

(30) Foreign Application Priority Data
Sep. 3, 2010  (GB) .................................. 1014657.9

(51) Int. Cl.
*G01J 3/10* (2006.01)
*G01N 21/67* (2006.01)
(Continued)

(52) U.S. Cl.
CPC . *G01J 3/10* (2013.01); *G01N 21/67* (2013.01); *G01J 3/443* (2013.01); *G01N 21/05* (2013.01)

(58) Field of Classification Search
CPC .......... G01N 21/67; G01N 21/05; G01J 3/443
USPC ........................................................ 356/313
See application file for complete search history.

(56) References Cited

U.S. PATENT DOCUMENTS 3,367,229 A * 2/1968 Berneron ....................... 356/313
3,569,767 A * 3/1971 Benson ...................... 313/231.51
(Continued)

FOREIGN PATENT DOCUMENTS

EP  0398462  11/1990
JP  08114549  5/1996
(Continued)

OTHER PUBLICATIONS

Boumans et al., "Influences of the physical and chemical processes in the electrode cavity and the gaseous atmosphere in the arc on the emission characteristics of the d.c. arc for spectrochemical analysis—I. Efficiency of particle transport from the electrode cavity to the excitation zone," Spectrochimica Acta, 24B, 585-610, 1969.
(Continued)

*Primary Examiner* — Kara E Geisel
(74) *Attorney, Agent, or Firm* — William R. McCarthy, III; Gordon Stewart

(57) ABSTRACT

A spark chamber for an optical emission analyser, comprising: a gas inlet located on a first side of the spark chamber for supplying a gas into the spark chamber; and a gas outlet located on a second side of the spark chamber arranged to convey the gas from the spark chamber; wherein an elongated electrode having an electrode axis generally along the direction of elongation is located within the spark chamber; and wherein: the first and second sides of the spark chamber lie at either side of the elongated electrode in directions generally perpendicular to the electrode axis; there is a gas flow axis through the spark chamber between the gas inlet and the gas outlet; and on passing along the gas flow axis from the gas inlet to the gas outlet the unobstructed internal cross sectional area of the spark chamber perpendicular to the gas flow axis remains constant to within a factor A, wherein A lies between 1.0 and 2.0

17 Claims, 5 Drawing Sheets

(51) Int. Cl.
G01J 3/443 (2006.01)
G01N 21/05 (2006.01)

(56) References Cited

U.S. PATENT DOCUMENTS

| | | | |
|---|---|---|---|
| 3,659,944 A | 5/1972 | Bojic | |
| 4,289,402 A | 9/1981 | Teubner | |
| 4,723,438 A | 2/1988 | Adler-Golden et al. | |
| 5,363,189 A | 11/1994 | Fukui et al. | |
| 5,699,155 A | 12/1997 | Sugihara | |
| 2004/0178917 A1* | 9/2004 | Duan | 340/632 |
| 2007/0165003 A1* | 7/2007 | Fux et al. | 345/171 |
| 2012/0236311 A1 | 9/2012 | Bettermann et al. | |

FOREIGN PATENT DOCUMENTS

| | | |
|---|---|---|
| JP | 2723455 | 3/1998 |
| JP | 11304708 | 11/1999 |

OTHER PUBLICATIONS

Charpak et al., "Location of the Position of a Spark in a Spark Chamber," Nucl. Inst. And Meth., 15, 318-322, 1962.

Chinese Office Action and Search Report issued Jun. 17, 2014, 16 pp.

Liu, "Spark Chamber," Atomic Energy Sciences and Technology, Issue 1, 14 pp., 1964.

Zou, "Research on a Spark Discharge Chamber," Acta Physica Sinica, 19(2), 9 pp., 1963.

* cited by examiner

SPARK CHAMBER FOR OPTICAL EMISSION ANALYSIS

FIELD OF THE INVENTION

This invention relates to the field of spark optical emission spectrometry. Specifically the invention is concerned with an improved spark chamber for an optical emission spectrometer.

BACKGROUND

Spark optical emission spectrometry is a well known technique used to analyse solid samples. Optical emission spectrometry may be conducted with either a spark or arc for example. For convenience, as used herein, the term spark optical emission spectrometry means any optical emission spectrometry employing an electrical discharge to excite the sample such as a spark or arc for example, and the term spark chamber means a chamber for conducting any electrical discharge. A solid sample is typically mounted onto the table of a spark stand, also known as Petrey's stand. The spark stand further comprises a spark chamber, within which is an electrode oriented to present a tapered end towards the sample surface. The table of the spark stand has an aperture in the spark chamber wall over which the sample is mounted, usually with an air-tight seal. The electrode is surrounded by an insulator except for its tapered end. A sequence of electrical discharges is initiated between the electrode and the sample, in which the sample acts as a counter electrode. The insulator promotes discharge to the sample rather than the chamber wall. Sample material local to the discharges is vaporised and a proportion of the vaporised atomic material is raised to excited states. On relaxing, the atomic material emits photons, the energies of which are characteristic of the elements in the material. Spectroscopic analysis of the emitted photons enables the composition of the sample material to be deduced. The spectroscopic analysis is conducted using an optical analyser which usually utilises a dispersive means such as a grating to disperse light spatially according to its wavelength. A detector, such as an array detector for example, is used to measure the quantity of light as a function of the degree of dispersion. Hence, a proportion of the light emitted during the discharges is transmitted from the spark chamber to the analyser for spectroscopic analysis.

To obtain information about a wide range of elements within samples, the instrument must be capable of transmitting photons below 190 nm from the spark stand to the detector, as some elements emit photons in the ultraviolet (UV) wavelength range when relaxing to a lower energy state. To avoid absorption of these UV photons by air and to avoid wavelength shifts associated with changes in the refractive index of gases (which changes with the pressure of the gas and the gas composition), the sample material is excited in the presence of an inert gas, typically argon, which is fed into the spark chamber at least during the time when the sequence of spark discharges is initiated. The presence of an inert gas also prevents oxidation of the sample surface.

The electrical discharges cause material to be ablated from the sample surface and some of this material is not in atomised form. Some much larger aggregates or particles of material are removed from the sample surface which are useless for the spectroscopic process, and are referred to as debris. This debris, along with the vaporised atomic material is liberated from the sample surface at each electrical discharge. To prevent cross contamination or so-called memory effects, preferably all the ablated material from one sample should be removed from the spark chamber before analysis of the next sample to eliminate any re-deposition of material from a preceding sample onto the next sample, and to prevent any such material from being present in the path of the electrical discharges. The argon gas which bathes the sample and the discharge path is utilised to sweep ablated materials including debris from the spark chamber in a continuous or semi-continuous process. Argon gas is typically arranged to flow into the spark chamber through at least one gas inlet and out of the spark chamber through at least one separate gas outlet, the flow of gas sweeping debris and vaporised material from the chamber. The gas flow is arranged to be present during the time when the sequence of electrical discharge is initiated. The gas flow may also be present during the time between sequences of electrical discharges. It is important to avoid debris and vaporised sample material from depositing on the surfaces of adjacent optics, which would impair the transfer of photons from the sample region to the optically dispersing element of the spectrometer. Should this occur, the spectrometer would have to be shut down whilst the optics were cleaned. In some spark chambers the gas is introduced along a tube leading from the spark chamber to the spectrometer optics, with the gas flow directed away from the optics in order to reduce the likelihood that material will pass from the spark chamber and be deposited upon the surfaces of the optics.

For analysis of the nitrogen content of a sample, outgassing of residual nitrogen from material at the internal surfaces of the walls of the spark chamber has been found to cause instability of the recorded nitrogen signal, and inaccuracy of the measured result with a high background nitrogen signal recorded after insertion of a new sample. Performing sequences of electrical discharges promotes the outgassing of nitrogen by heating and irradiating the material on the chamber walls with UV radiation. Several sequences of electrical discharges must be made on a sample before this residual nitrogen reduces sufficiently and this is undesirable for high throughput instruments in which precise and reliable nitrogen analysis is desired from the first run. The presence of a flow of argon gas reduces the time for the residual nitrogen to reduce.

Hence the argon gas is utilised for several purposes. However, argon and other inert gases are expensive and contribute to the running costs of the spectrometer and it is desirable that the lowest possible flow of inert gas is used which will be adequate for the purposes described above.

U.S. Pat. No. 3,815,995 describes a form of gas injection which is coaxial with the pin-like electrode used in the discharge process. This means of gas injection was designed to reduce the spread in positions over the sample surface over which repeated electrical discharges take place. However this prior art method suffers from poor evacuation of debris from the spark chamber.

CN 1796983A and CN 2769882Y describe a spark chamber comprising two gas inlets, each arranged to provide a gas flow adjacent the internal wall of the spark chamber. This promotes a circular flow of gas within the chamber. This arrangement suffers from the disadvantage that the cyclone-type gas flow generated carries particulate material towards the chamber walls, where it accumulates, rather than sweeping it from the chamber.

JP10160674A2 describes four gas inlets which direct gas in an inward radial direction towards the pin electrode. The symmetrical disposition of the gas inlets promotes a more stable electrical discharge, but again evacuation of debris is not efficiently accomplished.

EP00398462B1 describes the use of pulses of purge gas through the spark chamber to more efficiently remove debris in between the electrical discharges. However this method may promote after-pulsing of residual gas flow which could carry particulate debris towards the collection optics, and thereby contaminate them.

In view of the above, the present invention has been made.

SUMMARY OF INVENTION

According to an aspect of the present invention there is provided a spark chamber for an optical emission analyser, comprising: a gas inlet located on a first side of the spark chamber for supplying a gas into the spark chamber; and a gas outlet located on a second side of the spark chamber arranged to convey the gas from the spark chamber; wherein an elongated electrode having an electrode axis generally along the direction of elongation is located within the spark chamber; and wherein: the first and second sides of the spark chamber lie at either side of the elongated electrode in directions generally perpendicular to the electrode axis; there is a gas flow axis through the spark chamber between the gas inlet and the gas outlet; and on passing along the gas flow axis from the gas inlet to the gas outlet the unobstructed internal cross sectional area of the spark chamber perpendicular to the gas flow axis remains constant to within a factor A, wherein A lies between 1.0 and 2.0.

According to an additional aspect of the present invention there is provided a spark chamber for an optical emission analyser, comprising: a gas inlet located on a first side of the spark chamber for supplying a gas into the spark chamber; a gas outlet located on a second side of the spark chamber arranged to convey the gas from the spark chamber; and an elongated electrode having an electrode axis generally along the direction of elongation, located within the spark chamber; wherein: the first and second sides of the spark chamber lie at either side of the elongated electrode in directions generally perpendicular to the electrode axis; there is a gas flow axis through the spark chamber between the gas inlet and the gas outlet; and on passing along the gas flow axis from the gas inlet to the gas outlet the unobstructed internal cross sectional area of the spark chamber perpendicular to the gas flow axis remains substantially constant.

According to a further aspect of the present invention there is provided a method of optical emission spectrometry, comprising: providing a spark chamber, the spark chamber having a gas inlet located on a first side of the spark chamber for supplying a gas into the spark chamber and a gas outlet located on a second side of the spark chamber arranged to convey the gas from the spark chamber; arranging within the spark chamber an elongated electrode having an electrode axis generally along the direction of elongation; wherein the first and second sides of the spark chamber lie at either side of the elongated electrode such that there is a gas flow axis through the spark chamber between the gas inlet and the gas outlet which is generally perpendicular to the electrode axis; and wherein on passing along the gas flow axis from the gas inlet to the gas outlet the unobstructed internal cross sectional area of the spark chamber perpendicular to the gas flow axis remains constant to within a factor A, wherein A lies between 1.0 and 2.0.

The method of the present invention may comprise other, well known steps of optical emission spectrometry, such as any of the following: providing a solid sample for analysis, typically which is mounted such that it presents a surface of the sample to the end of the electrode and/or typically such that it lies over an aperture in the spark chamber wall, usually with an air-tight seal; causing one or more, typically a sequence of, electrical discharges between the electrode and the sample, in which the sample acts as a counter electrode; vaporising material from the sample and exciting at least a proportion of the vaporised material whereby the excited material emits photons, the energies of which are characteristic of the elements in the material; and performing spectroscopic analysis of the emitted photons to thereby enable the composition of the sample material to be deduced; wherein a gas, preferably such as argon, is fed into the chamber via the gas inlet during the analysis.

The spark chamber may be any shape such that the unobstructed cross sectional area perpendicular to the gas flow axis remains relatively constant as the gas travels generally along the gas flow axis from the gas inlet to the gas outlet. Preferably, on passing along the gas flow axis, where the spark chamber unobstructed internal dimensions reduce in one or more directions generally perpendicular to the gas flow axis, the spark chamber unobstructed internal dimensions increase in one or more other directions generally perpendicular to the gas flow axis so as to maintain a more constant unobstructed cross sectional area, i.e. within the factor A. Preferably the unobstructed internal cross sectional area of the spark chamber perpendicular to the gas flow axis remains constant to within a factor A, wherein A lies between 1.0 and 2.0. The value of A may lie between 1.0 and an upper limit selected from one of the following: 1.9, 1.8, 1.7, 1.6, 1.5, 1.4, 1.3, 1.2 and 1.1. More preferably A lies between 1.0 and 1.7. Even more preferably A lies between 1.0 and 1.4 and still even more preferably A lies between 1.0 and 1.3. Most preferably, the unobstructed internal cross sectional area of the spark chamber perpendicular to the gas flow axis remains substantially constant.

Preferably, the walls of the spark chamber, i.e. the radial walls (radially facing the electrode), are curved thereby defining an internal volume of the spark chamber with a curved outer shape. More preferably the nominal internal volume of the spark chamber is cylindrical, i.e. the walls define a cylindrical shape (cylindrical walls). Preferably, where the internal volume of the spark chamber is based upon a curved, more preferably cylindrical, shape, and therefore on travelling along the gas flow axis from inlet or outlet to the electrode the width of the spark chamber perpendicular to the gas flow axis expands due to the increasing distance from the flow axis to the curved side walls of the cylinder, the length (i.e. height) of the curved walls or cylinder decreases. In this type of embodiment, the elongated electrode is preferably oriented so that its axis lies approximately on the axis of the cylinder and the gas inlet and gas outlet are located in the curved walls of the chamber. Of course, the curvature of the walls of the chamber may be such that they form a single continuous wall, as in the case where the walls define a cylindrical shape for example.

The unobstructed internal cross sectional area of the spark chamber may be made to be constant within the factor A along the gas flow axis by manufacturing the spark chamber appropriately and/or introducing one or more components into the spark chamber to place a partial obstruction within the chamber. In preferred embodiments the insulator that substantially surrounds the elongated electrode is used to partially obstruct the gas flow within the spark chamber. The term unobstructed volume as used herein means a volume of space which is not obstructed by solid objects and which is able to be occupied by the gas flowing through the chamber. The unobstructed cross sectional area within the spark chamber is the cross sectional area which is unobstructed by solid objects and through which gas may flow. On travelling along the flow axis from the gas inlet to the gas outlet, the unobstructed internal cross sectional area of the spark chamber perpendicular to the gas flow axis is a measure of the gas flow resistance through the spark chamber. Unlike the prior art electrode insulators, the preferred insulator for use in the present invention is not rotationally symmetric about the electrode axis. Preferably, the insulator has a height which increases on travelling along the gas flow axis from inlet or outlet to the electrode. Thus, in the preferred embodiment of the cylindrically shaped spark chamber, as the width of the spark chamber perpendicular to the gas flow axis expands, the height of the insulator increases, thereby to maintain the unobstructed internal cross sectional area constant to within the factor A.

The gas inlet is one or more orifices in the first side of the spark chamber to which is connected a conduit supplying gas. Preferably the gas inlet is a single orifice in the first side of the spark chamber to which is connected a conduit supplying gas. The gas outlet is one or more orifices, preferably a single orifice, in the second side of the spark chamber to which is connected a conduit for conveying gas from the chamber. The orifices for the gas inlet and gas outlet may be any suitable shape. For example, the one or more orifices may be circular, ovoid, square, or rectangular in shape. Preferably, the one or more orifices comprise a rectangular orifice, especially each of the inlet and outlet consist of a single rectangular orifice. In a preferred embodiment of having a rectangular orifice for the gas inlet and/or outlet, more preferably the rectangular orifice has a height substantially equal to the height of the spark chamber at the inlet and/or outlet respectively.

The factor A is calculated by taking the ratio of the maximum of the unobstructed internal cross sectional area of the spark chamber perpendicular to the gas flow axis, $Area_{max}$, to the minimum of the unobstructed internal cross sectional area of the spark chamber perpendicular to the gas flow axis, $Area_{min}$, i.e. $Area_{max}/Area_{min}$, the maximum and minimum values being found along the flow axis from the gas inlet to the gas outlet. Where the gas inlet comprises a plurality of orifices, the unobstructed internal cross sectional area of the spark chamber perpendicular to the gas flow axis at the gas inlet is the sum of the cross sectional areas of the orifices. Similar considerations apply to the gas outlet when it comprises a plurality of orifices.

The elongated electrode may be of any cross sectional shape (i.e. in cross section transverse to the electrode axis), but is preferably cylindrical in shape with a tapered conical end which extends within the spark chamber towards a sample position. Preferably the elongated electrode is a pin-shaped electrode. The elongated electrode has an axis, herein referred to as the electrode axis, the axis extending generally along the direction of elongation and the electrode is oriented within the spark chamber so that the axis is directed towards the sample position. The electrode axis is preferably located substantially radially centrally in the spark chamber. In a preferred embodiment, the electrode axis also defines an axial direction of the spark chamber, with the gas flowing in a generally radial direction from the inlet on the first side of the spark chamber to the outlet on the second side of the spark chamber.

Preferably the spark chamber internal shape and components placed within the spark chamber are such that turbulence is substantially eliminated, as will be further described.

The term gas flow axis is used herein to describe a line which extends from the gas inlet to the gas outlet through the spark chamber, the line being generally in a direction of flow of gas which is provided via the gas inlet and which travels to the gas outlet. Since the first and second sides of the spark chamber, and thus the inlet and outlet, lie at either side of the elongated electrode in directions generally perpendicular to the electrode axis, the gas flow axis is generally perpendicular to the electrode axis. It is to be understood that the path taken by the gas is preferably not solely along the line of the gas flow axis; rather it is a preferable feature of the present invention that the gas flows in a laminar flow pattern from the gas inlet to the gas outlet, spreading substantially fully across the chamber in directions perpendicular to the gas flow axis as it flows from the gas inlet to the gas outlet, so as to sweep debris efficiently from the chamber. Hence the term gas flow axis is herein used to describe a general direction taken by the gas. The gas flow may split into two streams, so as to largely circumvent the pin-shaped electrode. The gas will typically flow over and around the pin-shaped electrode.

Preferably the spark chamber is substantially cylindrical and the electrode is located approximately on the axis of the cylinder. Preferably the gas inlet and the gas outlet are located on the curved internal walls of the cylinder and are on opposing sides of the cylinder, more preferably on substantially diametrically opposing sides. In some embodiments the gas flow axis may be curved as the gas inlet and the gas outlet are not diametrically opposed to each other on the chamber wall. Preferably the gas inlet and the gas outlet are diametrically opposed to each other on the chamber wall and the gas flow axis is straight.

It has been found by the present inventors that the geometry of the internal volume of the spark chamber strongly influences the efficiency with which particulate and vaporised materials are swept from the chamber volume. Typical prior art spark chambers possess gas inlet tubes which are of a relatively small diameter compared to the maximum unobstructed internal diameter of the spark chamber. A small diameter gas inlet has often been favoured in order to ensure that there is a high gas flow velocity through the inlet tube so as to prevent backstreaming of materials onto the collection optics of the analyser, which, as noted above, lie upstream of the spark chamber. The relatively small gas inlet tube terminates at the spark chamber abruptly. Examples of such prior art systems are found in U.S. Pat. Nos. 5,699,155, 4,289,402 and CN1796983A. In these prior art systems, the unobstructed internal cross sectional area of the spark chamber perpendicular to the flow axis increases rapidly from the gas inlet as the gas travels into the chamber, as the chamber is cylindrical in shape with the gas inlet terminating on one curved side of the cylinder. Typically the ratio of the maximum unobstructed internal cross sectional area of the spark chamber perpendicular to the flow axis to its minimum at the gas inlet is 2.5. There is an abrupt change in the resistance to flow of the gas immediately after passing into the spark chamber from the gas inlet and, due to the increase in unobstructed cross sectional area, the flow velocity drops rapidly. These effects frequently result in turbulence, eddying, generally rotational or re-circulating flow patterns, and stagnation. Such gas flow conditions promote the re-deposition of material within the spark chamber, especially onto the chamber walls, with the possibility of material back-streaming along the gas inlet tube and being deposited onto the light collection optics. Low gas flow rates together with recirculation can result in the residence time of metal vapours from the discharge process being sufficiently long such that condensation occurs upon exposed surfaces such as the chamber walls and the insulator. Material deposition on the surfaces of the optics, the insulator or the chamber walls results in an increase in instrument down time for maintenance. Furthermore, turbulent flow impairs the stability of the electrical discharge, which can result in reduced precision of measurement.

The inventors realised that in contrast to the gas flow conditions promoted by prior art spark chamber geometries, a laminar gas flow is highly desirable to counter these effects and, that to produce such a laminar gas flow, the unobstructed internal cross sectional area of the spark chamber should be relatively constant along the gas flow axis which passes from the gas inlet to the gas outlet. The gas inlet and gas outlet should terminate at the spark chamber with relatively large cross sectional areas so that the gas flow rate does not change abruptly in these regions. Multiple gas inlet and gas outlet orifices could be used to provide this characteristic, but preferably a single gas inlet orifice and a single gas outlet orifice is utilised. A single gas inlet orifice has the additional advantage that light from the discharge process may be efficiently transmitted along the gas inlet to the light collection optics of the spectrometer, especially so with a single gas inlet orifice having relatively large cross sectional area. Multiple inlet and/or outlet orifices may also promote areas in which turbulence and recirculation can occur, local to the inlet or outlet.

Utilisation of a spark chamber in which the unobstructed internal cross sectional area perpendicular to the gas flow axis remains relatively constant from the gas inlet to the gas outlet enables the present invention purge the spark chamber at significantly reduced rates of gas flow, yet with improved debris clearance characteristics. Typical prior art spark chambers utilise a 5 l/min gas flow rate; the present invention has allowed a 3 l/min gas flow rate to be used yet with superior purging characteristics. Lower gas flow rates result in lower running costs. The present invention may utilise any inert gas, as known in the art, preferably argon. The laminar flow characteristics provide less turbulence, less recirculation and hence less deposition and better debris clearance, resulting in less down time for cleaning the spark chamber, typically between two and three times lower. The laminar flow also promotes a more stable electrical discharge resulting in a higher level of reproducibility, leading to improved precision of analysis. As noted above, for analysis of the nitrogen content of a sample, outgassing of residual nitrogen from material at the internal surfaces of the walls of the spark chamber has been found to cause instability of the recorded nitrogen signal, and inaccuracy of the measured result, with high background nitrogen signal measured immediately after insertion of a sample. Appropriate choice of the inner wall chamber materials provided with a fine surface finish, suppression of dead or stagnant volumes plus a well designed argon flow pattern to efficiently rinse the chamber as provided by the present invention all promote outgassing of the residual nitrogen down to a level which allows to reach the necessary sensitivity and stability from the first run.

LIST OF FIGURES

DETAILED DESCRIPTION

Figure 1A:
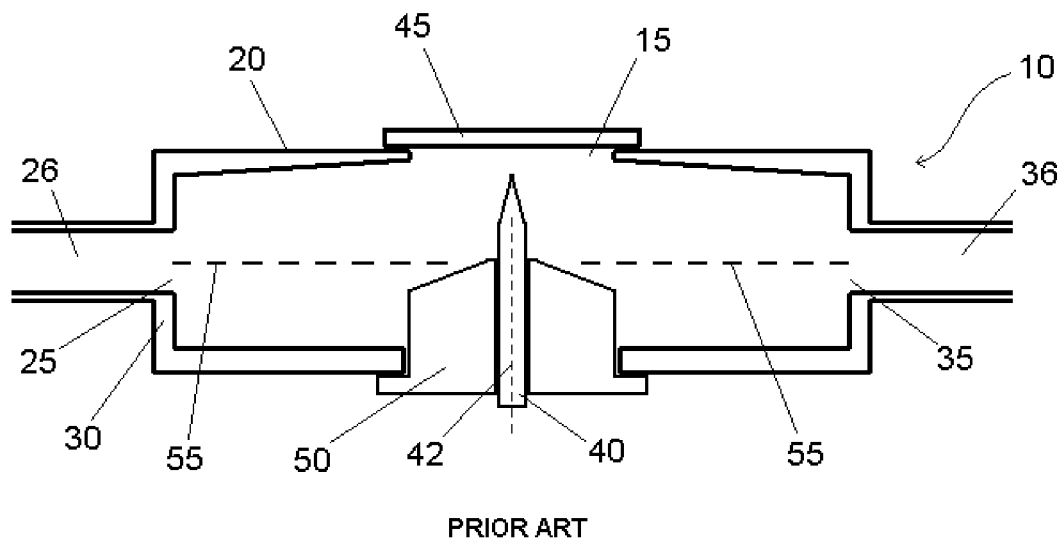
FIG. 1 shows schematic cross-sectional views of a prior art spark chamber.

FIG. 1a shows a schematic cross-sectional side view of a prior art spark chamber of generally cylindrical geometry 10, comprising an aperture 15 in the top face 20 of the chamber 10. Gas inlet 25 adjoins the chamber on a curved sidewall 30 and gas outlet 35 adjoins the chamber on an opposing side. Gas inlet conduit 26 connects to gas inlet 25; gas outlet conduit 36 connects to gas outlet 35. Within the chamber is an elongated cylindrical electrode 40, the tapered conical end of which faces the centre of aperture 15. The cylindrical electrode 40 has an axis 42. In use, a sample 45 is mounted onto the chamber so that a face of the sample covers aperture 15. An electrical discharge is initiated between the electrode 40 and the sample to vaporise sample material, as previously described. Argon gas of purity better than 99.997% is fed into the chamber via the gas inlet 25 at a rate of 5 slpm (standard litres per minute) during sample analysis. The maximum unobstructed internal cross sectional area of the spark chamber 10 perpendicular to the gas flow axis, $Area_{max}$, is some 2.5 times larger than the cross sectional area of the gas inlet 25, which is the minimum unobstructed internal cross sectional area of the spark chamber perpendicular to the gas flow axis, $Area_{min}$. Hence the factor A for this chamber is 2.5. Insulator 50 is located within the spark chamber and surrounds a portion of electrode 40 to prevent parasitic discharges to the internal chamber wall. Insulator 50 is rotationally symmetric about the electrode axis 42.

The gas flow through spark chamber 10 follows a gas flow axis 55 from near gas inlet 25 to near gas outlet 35. Gas conduit 26 and gas inlet 25 have cross sectional areas that are substantially smaller than the maximum unobstructed internal cross sectional area, $Area_{max}$, of the chamber 10. In this prior art chamber of FIG. 1a, the resistance to gas flow changes abruptly at gas inlet 25 and gas outlet 35 as the unobstructed internal cross sectional area perpendicular to the gas flow axis changes abruptly at gas inlet 25 and gas outlet 35.

Figure 1B:
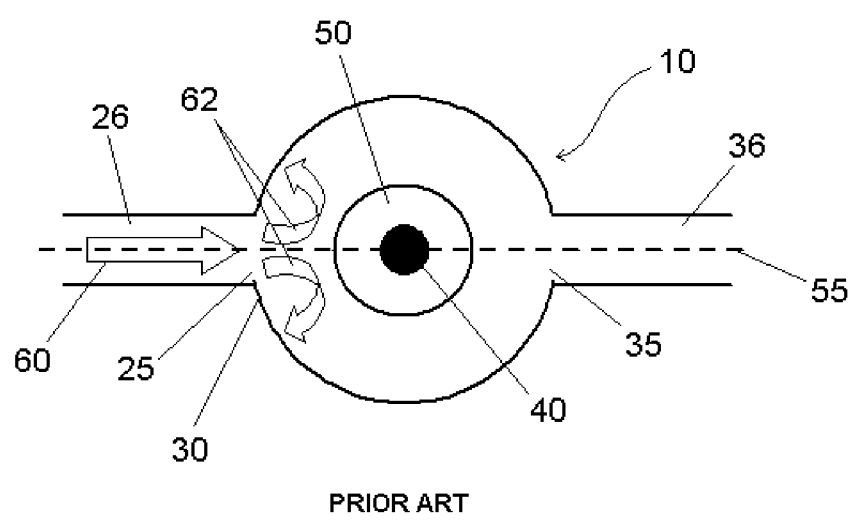

FIG. 1b is a schematic cross sectional top view of the chamber of FIG. 1a with like features bearing the same reference numerals. Gas flow into the chamber 10 is denoted by arrow 60. Due to the abrupt change in flow resistance in the vicinity of gas inlet 25, some gas recirculates, denoted by arrows 62. Recirculating gas 62 tends to deposit material onto the walls of chamber 10 and contributes to an increased residence time for material from the spark discharge process, encouraging condensation of some of the material upon the chamber and structures within the chamber.

Figure 2A:
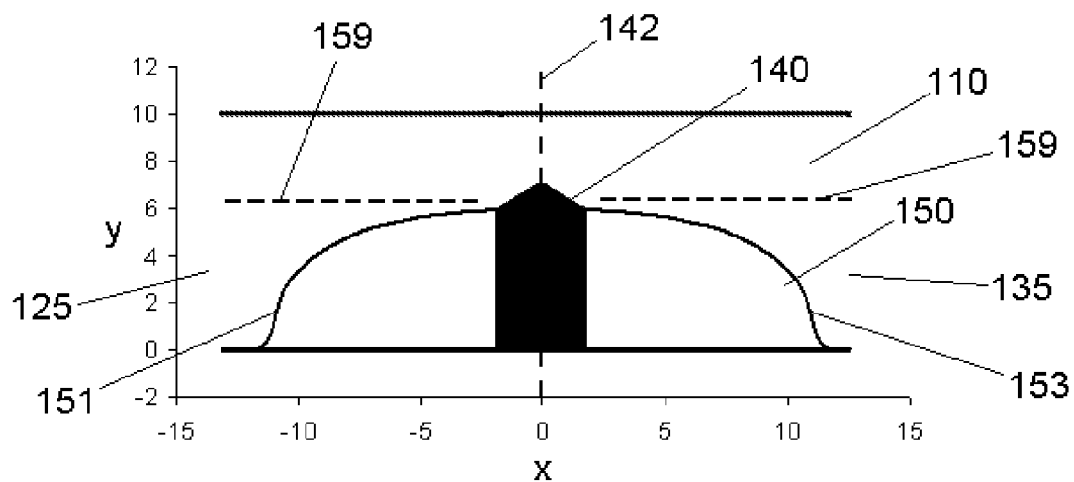
FIG. 2 shows schematic and scaled cross sectional views of insulators used within embodiments of the present invention.

An embodiment of the present invention utilises an insulator surrounding an elongated electrode to partially obstruct the internal volume of a cylindrical spark chamber in order to maintain a more constant unobstructed internal cross sectional area presented to the gas flow. FIG. 2a shows a cross sectional view of an insulator 150 according to such an embodiment, the cross sectional view having the section in a direction parallel to the gas flow axis. Cylindrical elongated electrode 140 has axis 142 within cylindrical shaped spark chamber 110, the axis 142 being approximately co-axial with the cylindrical shaped spark chamber. The top face of the chamber 110 has an aperture (not shown) to accommodate a sample in a similar manner to the prior art embodiment shown in FIG. 1. The y axis shows height of the chamber in mm and the x axis shows distance along the chamber from the gas inlet 125 to the gas outlet 135 in mm with the zero point located at the electrode axis 142. Gas inlet 125 and gas outlet 135 are of rectangular cross sectional shape of 10 mm in the y direction and 10 mm in the z direction (the z direction being perpendicular to the x and y directions and being out of the plane of FIG. 2a). The inlet and outlet have a height (in the y-direction) which is equal to the height of the spark chamber 110 at the inlet and outlet respectively. The insulator 150 is shaped so that the unobstructed internal cross sectional area perpendicular to the gas flow axis 159 (which is in the direction of the x axis) remains constant from the gas inlet 125 to the gas outlet 135, i.e. the unobstructed cross sectional area remains constant to a factor 1.0. As the insulator 150 has a rectangular cross section in the direction perpendicular to the gas flow axis, the insulator 150 is therefore not rotationally symmetrical. The insulator 150 with the shape parallel to the gas flow axis of FIG. 2a whilst having a rectangular cross section in the direction perpendicular to the gas flow axis is the theoretical optimum profile to maintain a constant cross section for the flow throughout the whole spark chamber 110, the chamber being cylindrical with diameter 26 mm and maximum initial height of 10 mm.

Figure 2B:
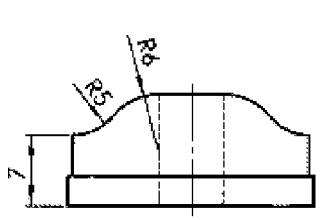
Figure 2C:
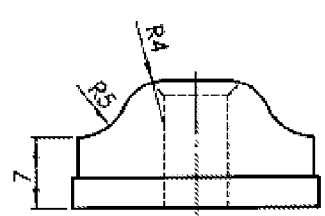
Figure 2D:
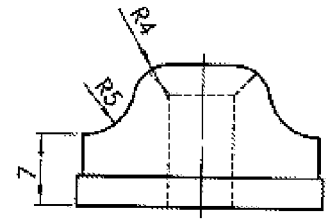

Whilst the insulator 150 with profile shown in FIG. 2a is an embodiment of the present invention, the inventors have found that more preferred embodiments follow the shapes depicted in FIG. 2b-2d. These insulators include a base of height 7 mm as depicted in the figure, which is located within the base of the chamber and the lower 7 mm of these insulators therefore lies below the y=0 line and is not within the chamber itself. These insulator profiles above the y=0 line avoid the steep increase and decrease in height depicted in FIG. 2a at 151 and 153. Insulator shapes depicted in FIGS. 2b-2d have smoothed leading and tailing faces, with differing heights to allow tailoring of the gas velocity at the spark location depending upon the application. As with the insulator 150 of FIG. 2a, the insulator profiles in FIGS. 2b-2d are not rotationally symmetric, rather they are cross sectional views through the insulators in a plane parallel to the gas flow axis. In the perpendicular plane to the gas flow axis, all the insulator profiles of FIGS. 2b-2d are rectangular in shape.

Figures 2E, 2F:
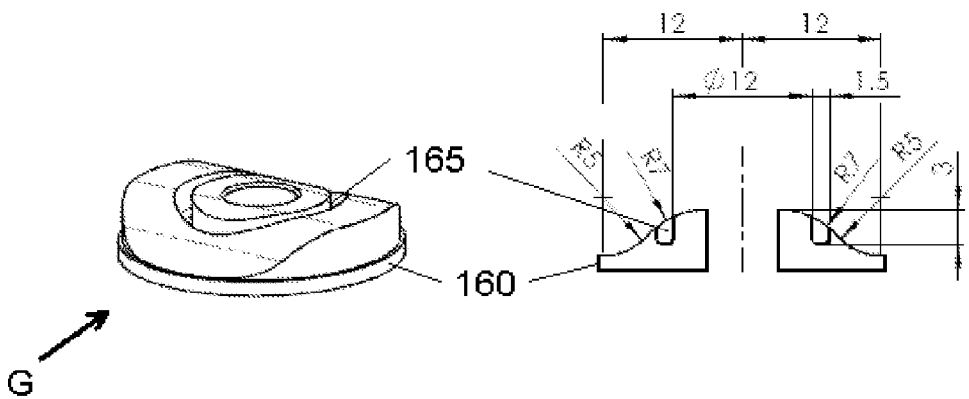

A further preferred embodiment utilises an insulator shape depicted in FIGS. 2e isometric, and 2f, sectional, views. The isometric view of FIG. 2e shows a similar general form to the insulators of FIGS. 2a-2d, wherein the profile in a section parallel to the gas flow axis is shaped, and the profile in a section perpendicular to the gas flow axis is rectangular, however the detailed dimensions differ. FIG. 2f shows the same insulator of FIG. 2e in a section parallel to the gas flow axis, the gas flow axis being denoted by direction G of FIG. 2e. The insulator of FIGS. 2e and 2f include a base 160 which lies below the y=0 line and hence is not within the chamber during its operation. The insulator depicted in FIGS. 2e and 2f also includes a groove, 165, known in the prior art to provide an area shadowed from metallization, the metallization being produced during the discharge process. This metallization would otherwise build up and tend to eventually provide a conductive path across the surface of the insulator between the electrode and the chamber wall. Other insulators such as those in FIGS. 2a-2d may also have such a groove, though it is not shown in those figures.

Figure 3:
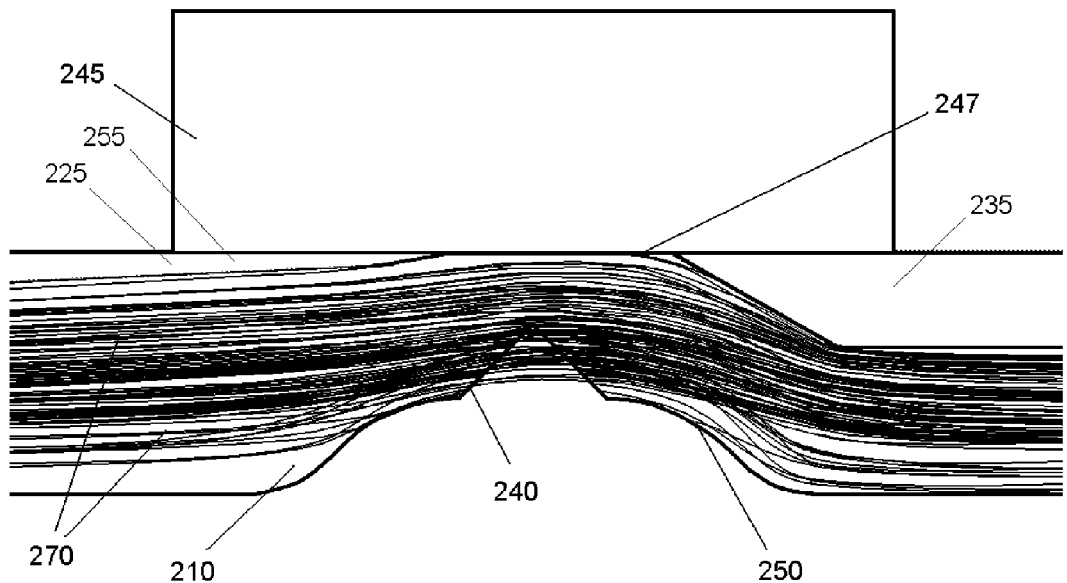
FIG. 3 shows Computational Fluid Dynamics flow results for gas flows within a spark chamber utilising the present invention.

Three-dimensional flow simulations using Computational Fluid Dynamics (CFD) have been performed upon a spark chamber utilising the present invention. FIG. 3 shows a cross sectional side view of a chamber 210. In this example, gas inlet 225 and gas outlet 235 are shown and the chamber 210 has been enlarged in region 255 to allow an enlarged gas inlet 225 to be used, so as to facilitate improved optical collection of photons. Sample 245 is attached to chamber 210 and presents sample surface 247 towards pin-shaped electrode 240. Insulator 250 surrounds the lower portion of electrode 240 to prevent parasitic discharge to the chamber walls, and is shaped according to the depiction in FIG. 2b. Flow lines 270 show the results of the CFD modelling, revealing substantially laminar flow through chamber 210. The present invention produces an improved laminar gas flow through the spark chamber in which the gas velocity is maintained to a nearly constant value. The accumulation of particulate debris and condensates is substantially reduced, resulting in reduced downtime of the instrument.

Figure 4A:
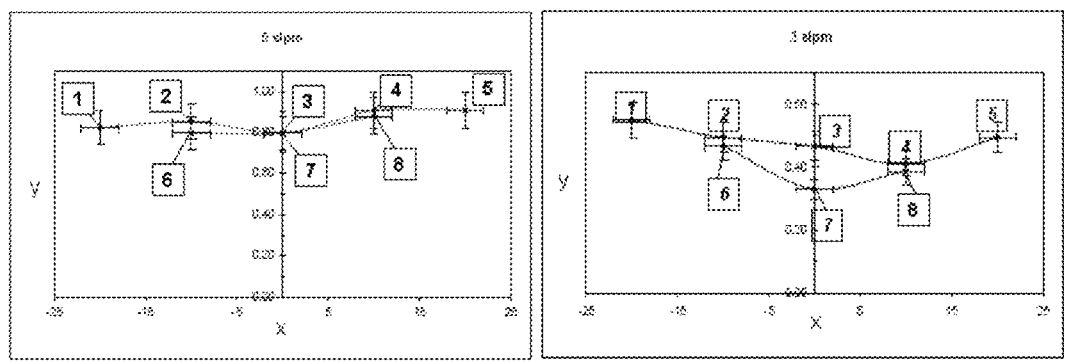
FIG. 4 shows results of measured particle velocities in gas flowing through a prior art spark chamber, together with a diagram showing locations within the chamber where measurements were made.
Figure 4B:
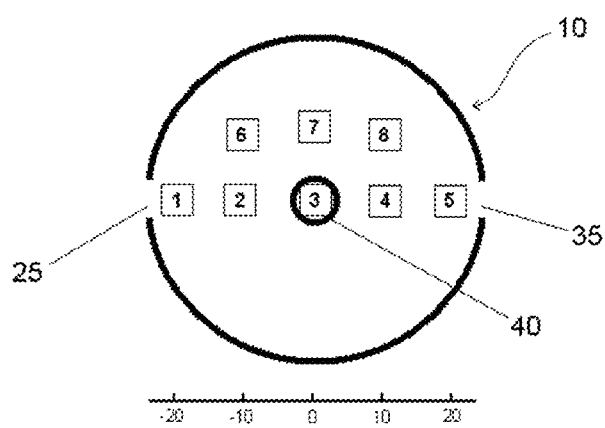

Experiments were performed to determine gas flow characteristics within a prior art spark chamber similar to that of FIG. 1. Particle tracers comprising 10 μm diameter hollow glass spheres were injected through a pipe terminated by a flat nozzle located within the gas inlet 25 and were carried by 1 slpm of gas flow. The remainder of the gas flow was directed through the gas inlet as normal. The spark chamber was fitted with a window instead of a sample to cover aperture 15. Outside the spark chamber a ring lamp was positioned to illuminate the inside of the spark chamber through the window. A short-exposure camera was mounted above the window and images recorded of the particle tracers whilst the gas was flowing through the chamber. At certain exposure times the image of the particles allowed measurement of the particle velocity at locations within the chamber. FIG. 4a is a graph showing particle velocity (y) in ms$^{-1}$ vs. position (x) within a prior art chamber, for gas flow rates of 5 slpm (left hand graph) and 3 slpm (right hand graph). Particle velocities were estimated at positions within the chamber 10 as denoted in FIG. 4b by numerals 1-8. Gas inlet 25, gas outlet 35 and pin-shaped electrode 40 are depicted schematically in FIG. 4b which also shows the x scale. Insulator 50 is not shown for clarity. It can be seen from FIG. 4a that the gas velocity along the gas flow axis which extends from gas inlet 25 to gas outlet 35 in a line along numerals 1-5 remains relatively constant for a gas flow rate of 5 slpm, and that the gas velocity following a path marked by numerals 6-8 also remains relatively constant and maintains a velocity of ~0.9 ms$^{-1}$. However if the gas flow rate is reduced, to conserve gas, to 3 slpm, the gas velocity drops to ~0.5 ms$^{-1}$ along the gas flow axis, and drops below this to 0.35 ms$^{-1}$ at location denoted by numeral 7.

Figure 5A:
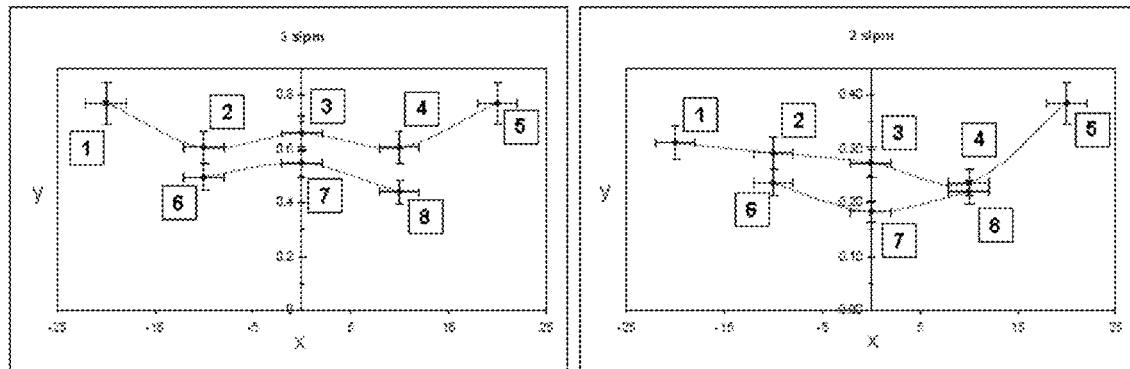
FIG. 5 shows results of measured particle velocities in gas flowing through a spark chamber within which are three different insulators shaped according to the present invention.
Figure 5B:
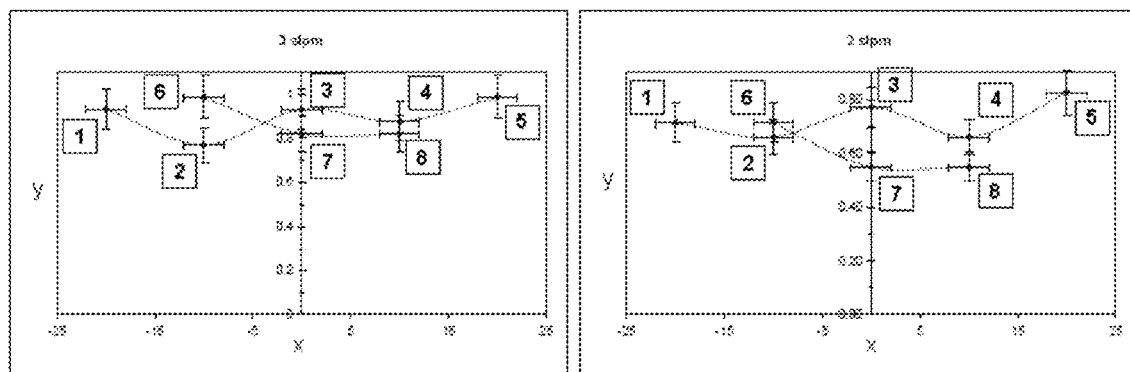
Figure 5C:
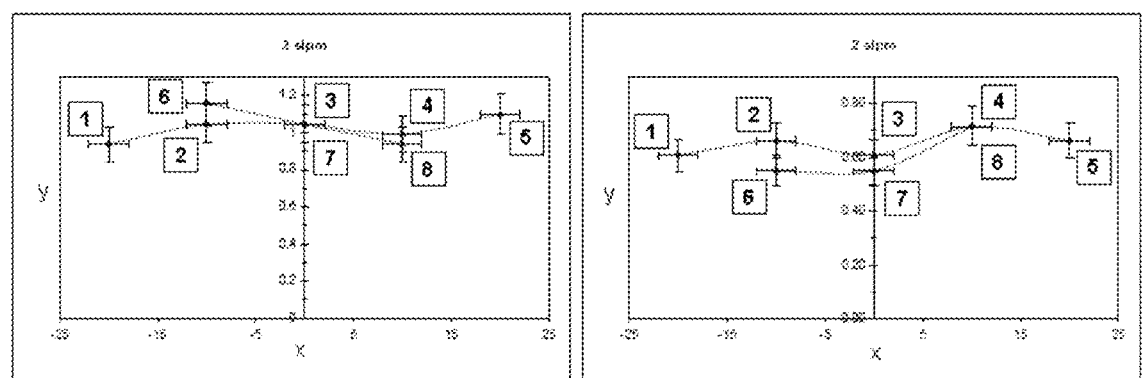

FIG. 5 shows graphs showing particle velocity (y) in ms$^{-1}$ vs. position (x) within a chamber utilising the present invention, for gas flow rates of 3 slpm (left hand graphs) and 2 slpm (right hand graphs). FIG. 5a results relate to an embodiment using the insulator depicted in FIG. 2b; FIG. 5b results relate to an embodiment using the insulator depicted in FIG. 2c and FIG. 5c results relate to an embodiment using the insulator depicted in FIG. 2d. Particle velocities were estimated at positions within the chamber as denoted in FIG. 4b by numerals 1-8. It can be seen that for the insulators depicted in FIGS. 2c and 2d, particle velocities of ~0.9 ms$^{-1}$ or greater are attained at a flow rate of only 3 slpm. Furthermore, for the insulators depicted in FIGS. 2c and 2d, the particle velocities are significantly greater at a flow rate of only 2 slpm compared to the prior art design at a flow rate of 3 slpm. For the insulator depicted in FIG. 2b, the particle velocities are again greater compared to the prior art design at the same flow rate of 3 slpm. Furthermore, the particle velocities are relatively constant at all positions within the chamber for these flow rates.

It will be appreciated that whilst preferred embodiments tailor the internal volume of the spark chamber by partially filling it with a shaped insulator, alternative embodiments could utilise shaped walls to the chamber or other components introduced into the chamber to partially obstruct the gas flow. The shape of the components will vary if the overall geometry of the spark chamber varies.

As used herein, including in the claims, unless the context indicates otherwise, singular forms of the terms herein are to be construed as including the plural form and vice versa. For instance, unless the context indicates otherwise, a singular reference herein including in the claims, such as "a" or "an" means "one or more".

Throughout the description and claims of this specification, the words "comprise", "including", "having" and "contain" and variations of the words, for example "comprising" and "comprises" etc, mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

The use of any and all examples, or exemplary language ("for instance", "such as", "for example" and like language) provided herein, is intended merely to better illustrate the invention and does not indicate a limitation on the scope of the invention to unless otherwise claimed. No language in the specification should be construed as indicating any non-claimed element as essential to the practice of the invention.

The invention claimed is:

1. A spark chamber for an optical emission analyser, comprising:
   (1) a gas inlet located on a first side of the spark chamber for supplying a gas into the spark chamber; and
   (2) a gas outlet located on a second side of the spark chamber arranged to convey the gas from the spark chamber;
   wherein an elongated electrode having an electrode axis generally along a direction of elongation is located within the spark chamber; and wherein:
   (a) the first and second sides of the spark chamber lie at either side of the elongated electrode in directions generally perpendicular to the electrode axis;
   (b) there is a gas flow axis through the spark chamber between the gas inlet and the gas outlet and;
   (c) on passing along the gas flow axis from the gas inlet to the gas outlet an unobstructed internal cross sectional area of the spark chamber perpendicular to the gas flow axis remains constant to within a factor A, wherein A lies between 1.0 and 2.0.

2. The spark chamber of claim 1 wherein A lies between 1.0 and an upper limit selected from one of the following: 1.9, 1.8, 1.7, 1.6, 1.5, 1.4 1.3, 1.2 and 1.1.

3. The spark chamber of claim 1 wherein the spark chamber contains a component shaped so as to make the unobstructed internal cross sectional area of the spark chamber perpendicular to the gas flow axis constant to within the factor A.

4. The spark chamber of claim 3 wherein the component is an insulator substantially surrounding the elongated electrode.

5. The spark chamber of claim 4 wherein the insulator is not rotationally symmetric about the electrode axis.

6. The spark chamber of claim 5 wherein the insulator has a height which is perpendicular to the gas flow axis, and wherein the height increases along the gas flow axis from the gas inlet to the elongated electrode and decreases along the gas flow axis from the elongated electrode to the gas outlet.

7. The spark chamber of claim 1, wherein the internal volume of the spark chamber is defined by cylindrical walls, and the elongated electrode lies approximately on the axis of the cylinder.

8. The spark chamber of claim 7 wherein the gas inlet and outlet lie on the walls of the cylinder.

9. The spark chamber of claim 1, wherein a gas flow direction is curved.

10. The spark chamber of claim 1, wherein the gas inlet and/or outlet are rectangular in shape.

11. The spark chamber of claim 10 wherein the gas inlet and/or outlet have a height substantially equal to the height of the spark chamber at the inlet and/or outlet.

12. The spark chamber of claim 3 wherein the component comprises a substantially shaped profile in a section parallel to the gas flow axis and a substantially rectangular profile in a section perpendicular to the gas flow axis.

13. The spark chamber of claim 7 where on travelling along the gas flow axis from the gas inlet or gas outlet towards the electrode, a height of the spark chamber perpendicular to the gas flow axis reduces as the distance from the gas flow axis to the cylindrical walls of the spark chamber increases.

14. A method of optical emission spectrometry, comprising:
   providing a spark chamber, the spark chamber having a gas inlet located on a first side of the spark chamber for supplying a gas into the spark chamber and a gas outlet located on a second side of the spark chamber arranged to convey the gas from the spark chamber; arranging within the spark chamber an elongated electrode having an electrode axis generally along a direction of elongation;
   wherein the first and second sides of the spark chamber lie at either side of the elongated electrode such that there is a gas flow axis through the spark chamber between the gas inlet and the gas outlet which is generally perpendicular to the electrode axis; and wherein on passing along the gas flow axis from the gas inlet to the gas outlet an unobstructed internal cross sectional area of the spark chamber perpendicular to the gas flow axis remains constant to within a factor A, wherein A lies between 1.0 and 2.0.

15. A method according to claim 14, additionally comprising detecting an optical emission from the spark chamber.

16. A method of optical emission spectroscopy, comprising directing a gas flow from a gas inlet located on a first side of a spark chamber to a gas outlet located on a second side of the spark chamber, the inlet and outlet positioned on either side of an elongated electrode having an electrode axis generally along a direction of elongation, such that on passing along a gas flow axis from the gas inlet to the gas outlet an unobstructed internal cross sectional area of the spark chamber perpendicular to the gas flow axis remains constant to within a factor A, wherein A lies between 1.0 and 2.0.

17. A method according to claim 14, additionally comprising detecting an optical emission from the spark chamber.

* * * * *

UNITED STATES PATENT AND TRADEMARK OFFICE
CERTIFICATE OF CORRECTION

PATENT NO.        : 9,127,982 B2
APPLICATION NO.   : 13/817001
DATED             : September 8, 2015
INVENTOR(S)       : Jean-Luc Dorier et al.

Page 1 of 1

It is certified that error appears in the above-identified patent and that said Letters Patent is hereby corrected as shown below:

Title Page, Col. 2, line 16, item (57) in the Abstract, Delete "2.0" and insert -- 2.0. --, therefor.

In the Claims

In Claim 2, Column 11, line 47, Delete "1.4" and insert -- 1.4, --, therefor.

Signed and Sealed this
Twenty-third Day of August, 2016

Michelle K. Lee
*Director of the United States Patent and Trademark Office*